(12) United States Patent
Koivisto et al.

(10) Patent No.: US 10,750,963 B2
(45) Date of Patent: Aug. 25, 2020

(54) APPARATUS AND METHOD FOR HEARTBEAT DETECTION

(71) Applicant: Suunto Oy, Vantaa OT (FI)

(72) Inventors: Tero Koivisto, Turku (FI); Mikko Pänkäälä, Turku (FI); Tapani Nevalainen, Turku (FI)

(73) Assignee: Suunto Oy, Vantaa (FI)

( * ) Notice: Subject to any disclaimer, the term of this patent is extended or adjusted under 35 U.S.C. 154(b) by 120 days.

(21) Appl. No.: 15/915,090

(22) Filed: Mar. 8, 2018

(65) Prior Publication Data

US 2018/0256040 A1  Sep. 13, 2018

(30) Foreign Application Priority Data

Mar. 9, 2017 (FI) .................................... 20175219
Mar. 9, 2017 (GB) .................................. 1703747.4

(51) Int. Cl.
| | |
|---|---|
| *A61B 5/02* | (2006.01) |
| *A61B 5/0245* | (2006.01) |
| *A61B 5/0456* | (2006.01) |
| *A61B 5/00* | (2006.01) |
| *A61B 5/0402* | (2006.01) |

(52) U.S. Cl.
CPC ........ *A61B 5/0245* (2013.01); *A61B 5/04028* (2013.01); *A61B 5/0456* (2013.01); *A61B 5/7225* (2013.01)

(58) Field of Classification Search
CPC . A61B 5/0245; A61B 5/04028; A61B 5/0456; A61B 5/7225
See application file for complete search history.

(56) References Cited

U.S. PATENT DOCUMENTS

| | | | |
|---|---|---|---|
| 4,250,889 | A | 2/1981 | Levin |
| 5,957,857 | A | 9/1999 | Hartley |
| 6,377,844 | B1 | 4/2002 | Graen |
| 2012/0310051 | A1 | 12/2012 | Addison et al. |
| 2014/0163386 | A1 | 6/2014 | He et al. |
| 2014/0358012 | A1 | 12/2014 | Richards et al. |
| 2016/0143549 | A1 | 5/2016 | Tsuchimoto et al. |
| 2016/0210987 | A1 | 7/2016 | Sugiyama |

FOREIGN PATENT DOCUMENTS

GB          2460759 A     12/2009

*Primary Examiner* — Amanda K Hulbert
(74) *Attorney, Agent, or Firm* — Laine IP Oy

(57) ABSTRACT

According to an example aspect of the present invention, there is provided an apparatus for heartbeat detection, comprising: means for forming a first amplified signal and a second amplified signal on the basis of an input signal representative of heartbeat, means for forming a third signal by inverting the second signal and adding a base voltage, and means for indicating an overlap of the first signal and the third signal.

20 Claims, 4 Drawing Sheets

APPARATUS AND METHOD FOR HEARTBEAT DETECTION

FIELD

The present invention relates to heartbeat detection.

BACKGROUND

There are a number of different devices and methods for measuring, calculating or estimating the heart rate of a person. For example, heart rate monitors and similar wristop computers may include a transmitter belt attached to the human body by a flexible belt for detecting the heartbeat. Heartbeat detection may e.g. take place during motion of the person. The detection device equipped with electrodes transmits measurement data wirelessly to e.g. a wristwatch-like wristop computer, in which at least a part of the received signal is processed and displayed on the display of the wristop computer.

Heartbeat detection may be arranged by a topology in which signal derived from electrodes is amplified and filtered before analog-to-digital (AD) conversion. The digital signal is then provided for digital processing for heartbeat detection. However, since the analogue signal comprises disturbance, considerable digital signal processing may be required to recover appropriate data for heartbeat detection. Analogue electronics may be applied to process the analogue signal for removing disturbance.

US2014/0163386 discloses a circuit and method for electrocardiogram (ECG) monitoring. The method comprises: amplifying a signal from a signal source to form an amplified signal; amplifying the amplified signal with an amplifier having a bandwidth sufficient to form a filtered amplified signal with highest frequency pulsatile features of amplified signal preserved; amplifying the amplified signal with an amplifier having a bandwidth sufficient to preserve the baseline while removing the pulsatile components; adding a DC offset to the baseline to form an offset baseline; comparing the filtered amplified signal to the offset baseline; and generating an output signal if the filtered amplified signal is greater than the offset baseline.

SUMMARY OF THE INVENTION

The invention is defined by the features of the independent claims. Some specific embodiments are defined in the dependent claims.

According to a first aspect of the present invention, there is provided an apparatus for heartbeat detection, comprising: means for forming a first amplified signal and a second amplified signal on the basis of an input signal representative of heartbeat, means for forming a third signal by inverting the second signal and adding a base voltage, and means for indicating an overlap of the first signal and the third signal for detecting R wave.

According to a second aspect of the present invention, there is provided a method, comprising: forming a first amplified signal and a second amplified signal on the basis of an input signal representative of heartbeat, forming a third signal by inverting the second signal and adding a base voltage, and indicating an overlap of the first signal and the third signal.

According to an embodiment, the second amplified signal is formed by a first amplifier for amplifying an input heartbeat signal and the first amplified signal is formed by a second amplifier connected to an output of the first amplifier.

According to an embodiment, the third signal is formed by a third amplifier connected to an output of the first amplifier and to a base voltage source.

According to an embodiment, the overlap is indicated by a first comparator connected to an output of the second amplifier and to an output of the third amplifier, wherein the first comparator indicates R wave in response to the overlap.

According to an embodiment, an S wave is detected on the basis of the third signal and indicated for confirming the R wave detection.

EMBODIMENTS

Figure 1:
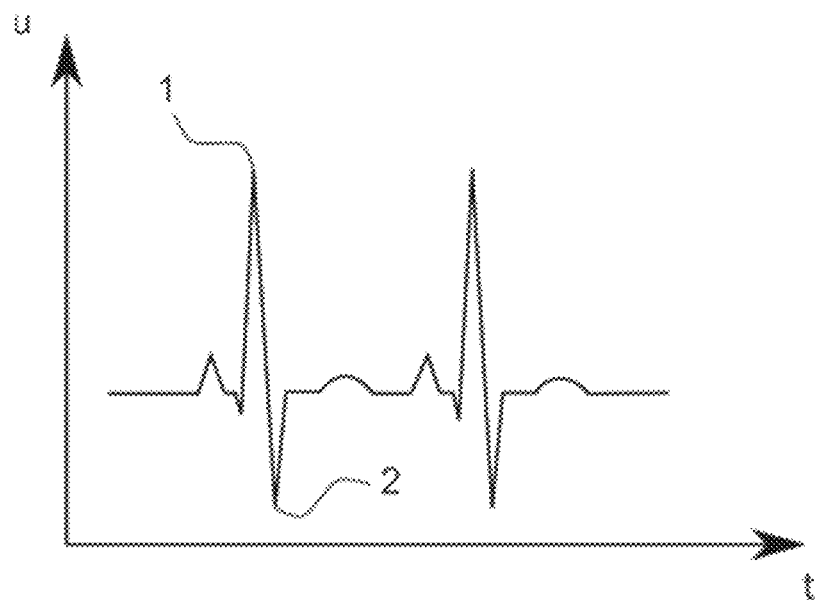
FIG. 1 illustrates a heartbeat signal.

FIG. 1 illustrates an example heartbeat signal, comprising an R wave 1 and an S wave 2. For applications employing a wearable heart monitor, generally only the R wave timing is relevant. Although the R wave 1 is easy to detect in ideal conditions, the detection may be challenging particularly when the person is in motion. Typical amplitude of a heartbeat signal is between 1 to 5 mV, so substantial initial amplification is needed. Movements of the detection device electrodes may cause strong disturbance on the signal and the R wave 1 amplitude may be less than that of disturbance caused by motion.

There is now provided an improved apparatus and method for heartbeat detection, enabling improved detection of R waves from input signal with high amount of disturbances.

Figure 2:
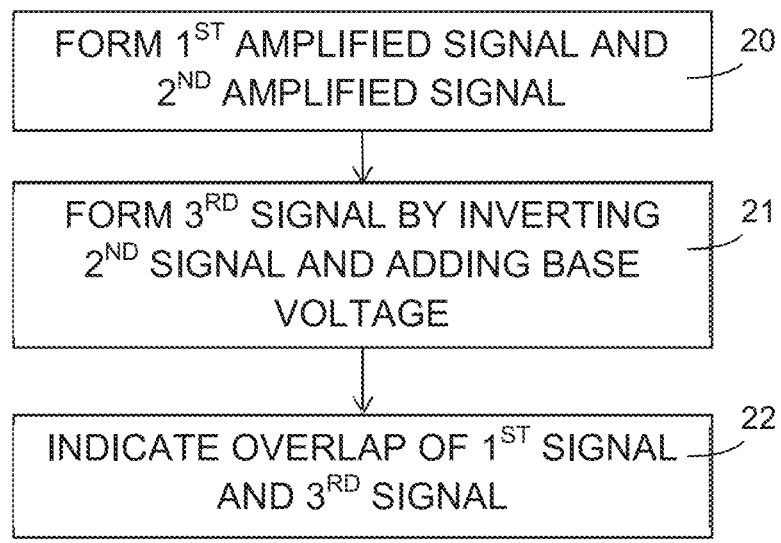
FIG. 2 illustrates functional blocks according to at least some embodiments of the present invention.

FIG. 2 illustrates functional blocks for an apparatus and a method for heartbeat detection according to at least some embodiments of the present invention. A first amplified signal and a second amplified signal is formed 20 on the basis of an input signal representative of heartbeat. A third signal is formed 21 by inverting the second signal and adding a base voltage. Overlap of the first signal and the third signal is indicated 22.

Figure 3A:
FIGS. 3a to 3d illustrate example signals processed according to at least some embodiments of the present invention.
Figure 3C:
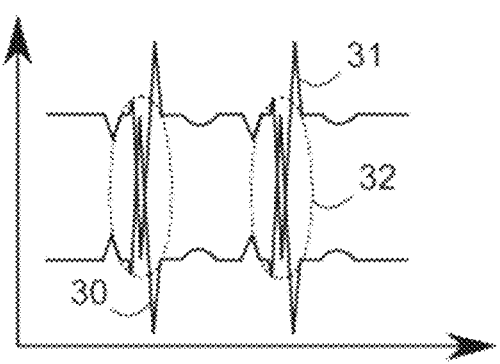
Figure 3B:
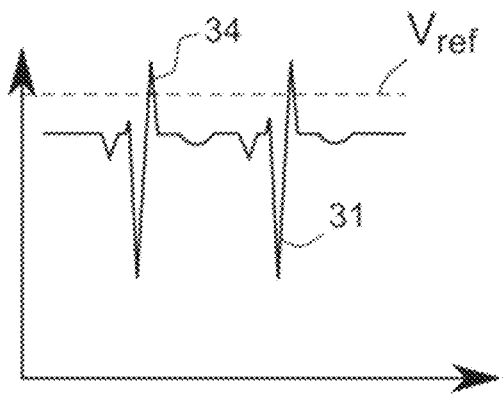
Figure 3D:
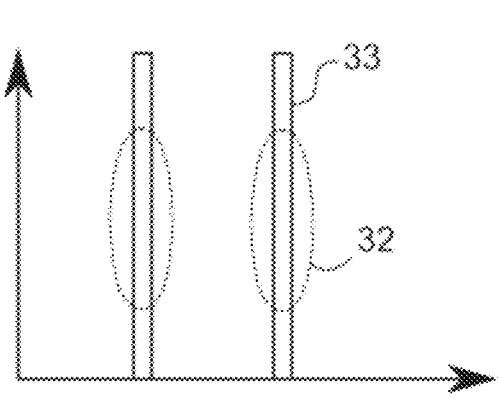

With reference to FIGS. 3a to 3d, FIG. 3a illustrates an example of the first signal 30 and 3b of the third signal 31. As illustrated in FIG. 3c, the signals 30, 31 are guided to an element detecting overlap of the signals in the area 32. The overlap in the area 32 may be indicated 33 as output as illustrated in FIG. 3d. By appropriate setting of the base voltage, the first signal and the third signal overlap when the R wave is present.

Features 20-22 may be implemented by reliable analogue components on a simple integrated circuit requiring less space than known detection circuits, which is particularly advantageous for portable detection devices.

Figure 4:
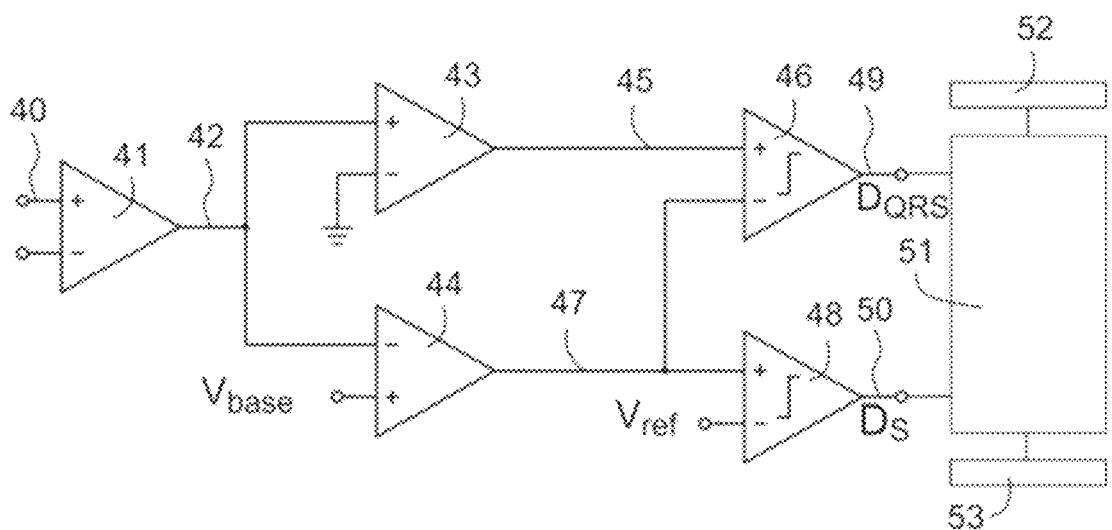
FIG. 4 illustrates an example apparatus capable of supporting at least some embodiments of the present invention.

FIG. 4 illustrates an example apparatus comprising a circuit capable of supporting at least some embodiments of the present invention. The apparatus comprises a first amplifier 41 for amplifying an input heartbeat signal 40 from electrodes sensing the electric heartbeat signal from an object. An electrode element may be applied against the chest, neck, wrist, auricle or foot of a person, for example.

A second amplifier 43 is connected to an output 42 of the first amplifier 41. Output of the second amplifier 43 may form the first signal which is connected to a first comparator 46.

The apparatus further comprises a third amplifier 44 connected to the output 42 of the first amplifier 41 and to a base voltage source $V_{base}$. The third amplifier 44 forms 21 the third signal based on the second signal from the first amplifier 41.

The means or block 22 for indicating the overlap may comprise the first comparator 46 which is also connected to an output of the third amplifier 44. The first comparator 46 indicates in its output 49 R wave detection in response to the signals 45 and 47 overlapping.

Some or all of the amplifiers 41, 43, 44 may be programmable-gain amplifiers (PGA). The gain may be adjustable between 10-20 dB, for example. Some or all of the amplifiers 41, 43, 44 may filter the signal. The detection apparatus should cover bandwidth of around 0.5 to 150 Hz.

It is to be noted that in an alternative embodiment the first amplifier 41 is omitted and the input signal 40 is amplified by the amplifiers 43, 44. In this embodiment, the amplifier 44 may form 20 the second amplified signal, add the base voltage and invert the second signal to form 21 the third signal.

In some embodiments, the apparatus further comprises means for confirming the R wave detection on the basis of S wave detection. The S wave may be detected on the basis of the third signal and indicated for confirming the R wave detection. FIG. 4 further illustrates an embodiment for implementing such means. The apparatus may comprise a second comparator 48 connected to the output 47 of the third amplifier 44 and a reference voltage source $V_{ref}$ providing a threshold voltage for detecting an S wave exceeding the threshold voltage. Reference is also made to FIG. 3b illustrating the $V_{ref}$ and detection 34 of the S wave.

The presently disclosed features enable more reliable R wave detection for signals with high disturbance, particularly advantageous during physical exercise with high amount of disturbance caused by constant motion and motion changes. In some such situations the first signal and the second signal may sometimes overlap also outside actual R wave instances. The S wave based confirmation further improves detection accuracy in such situations.

The first and third signals 30, 31 need to be sufficiently separated from each other for enabling reliable R wave detection. Reliable S wave detection requires enough space between the $V_{base}$ and the power supply voltage $V_{dd}$. Preferably, the operating voltage is between 20%-40% of the $V_{dd}$ and $V_{base}$ is between 60%-80% of the $V_{dd}$. $V_{ref}$ needs to be high enough to enable the second comparator 48 to detect the S wave from the third signal 31, 47. For example, if 1.2 V supply power is used, 300 mV operating voltage may be used, $V_{base}$ may be 800 mV, and $V_{ref}$ may be 825 mV, for example. However, it will be appreciated that various other voltage levels may be selected, with appropriate relation between the values enabling adequate detection accuracy, such as adequate difference between the $V_{base}$ and the $V_{ref}$ enabling reliable detection of the S wave.

The apparatus may further comprise a processor or microcontroller 51 connected directly or indirectly to the output 49 of the first comparator. The processor may comprise at least one application-specific integrated circuit, ASIC. The processor may comprise at least one field-programmable gate array, FPGA. The processor may be means for performing method steps in the device. The processor may be configured, at least in part by computer instructions, to perform actions.

The apparatus may comprise memory 52. The memory may comprise random-access memory and/or permanent memory. The memory may comprise at least one RAM chip. The memory may be at least in part accessible to the processor 51. The memory may be at least in part comprised in the processor 51. The memory 52 may be means for storing information. The memory may comprise computer instructions that the processor is configured to execute. When computer instructions configured to cause the processor to perform certain actions are stored in the memory, and the device in overall is configured to run under the direction of the processor using computer instructions from the memory, the processor may be considered to be configured to perform said certain actions. The memory may be at least in part comprised in the processor.

The processor 51 may be configured to detect start time and end time of R wave on the basis of the indication 33 of the overlap.

Figure 5:
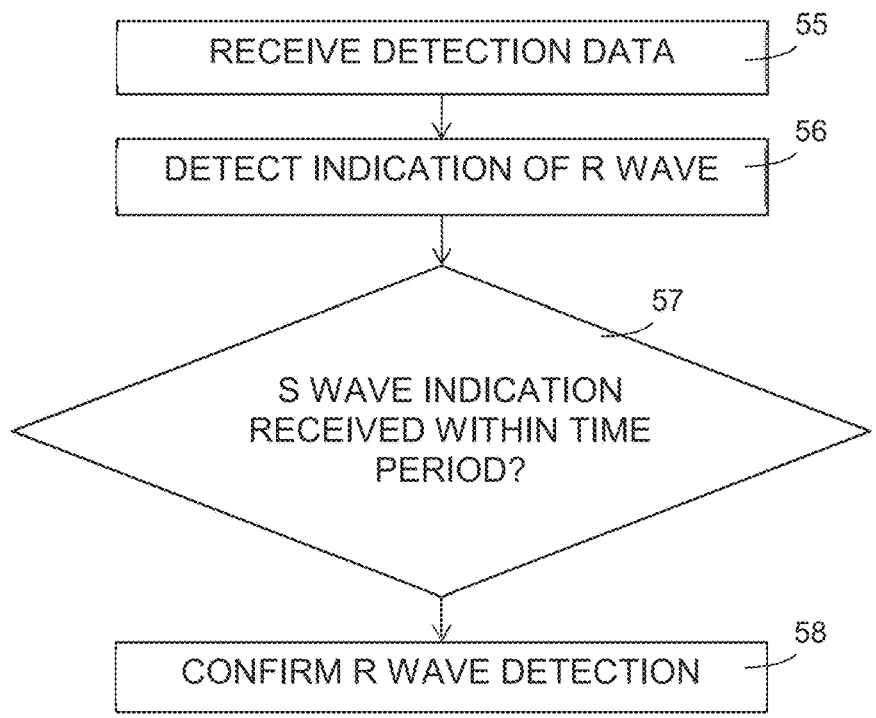
FIG. 5 illustrates a method according to some embodiments of the present invention.

The processor 51 may be connected also to the output 50 of the second comparator 48. The processor may be configured to perform a method for R wave detection based on S wave indication, illustrated in FIG. 5. The processor receives 55 detection data from the first comparator 46 indicating 22 the overlap and detects 56 time of indication of R wave. The processor may be configured to detect time of S wave on the basis of the indication from the second comparator 48 and compare to the time of R wave detection. For example, the processor may compare the R wave detection and S wave detection start times.

The processor 51 may be configured to confirm 58 the R wave in response to the S wave being detected 57 within a predetermined time period after the R wave indication. The processor may thus define occurrence time of the R wave in the middle of the start time and the end time indication from the first comparator 46 and store the occurrence value after the confirmation in the memory 52 and prepare. It is to be noted that although the method of FIG. 5 was explained in connection with the circuit of FIG. 4, the method may be applied also in connection with other circuits providing R wave indication and S wave indication.

The processor 51 may be configured to perform also other features, such as process the signal further, control the gain of PGAs in the circuit and/or control other functions of the apparatus.

The apparatus may comprise a communications unit 53, such as a wireless transmitter or a transceiver. Such wireless communications unit may be configured to transmit and receive, respectively, information in accordance with at least one cellular or non-cellular standard. The communications unit may be configured to operate in accordance with global system for mobile communication, GSM, wideband code division multiple access, WCDMA, long term evolution, LTE, 3GPP new radio access technology (N-RAT), IS-95, wireless local area network, WLAN, Ethernet and/or worldwide interoperability for microwave access, WiMAX, standards, for example. The apparatus or the communications unit 53 may comprise a near-field communication, NFC, transceiver 140 for transmitting the heartbeat information to another apparatus, such as a wristwatch or a mobile communications device. The NFC transceiver may support at least one NFC technology, such as NFC, Bluetooth, Wibree or similar technologies. The apparatus may in some application embodiments also comprise further units, such as a user interface and/or one or more further sensors.

The apparatus illustrated above may be provided with further elements and functions not illustrated in FIG. 4. For example, the apparatus may be provided with further analogue or digital filtering to further reduce disturbance caused by motion.

There are a number of different devices and methods for measuring, calculating or estimating the heart rate of a person in which embodiments of the present invention may be applied. Heartrate measurement may e.g. take place during motion of the person.

Figure 6:
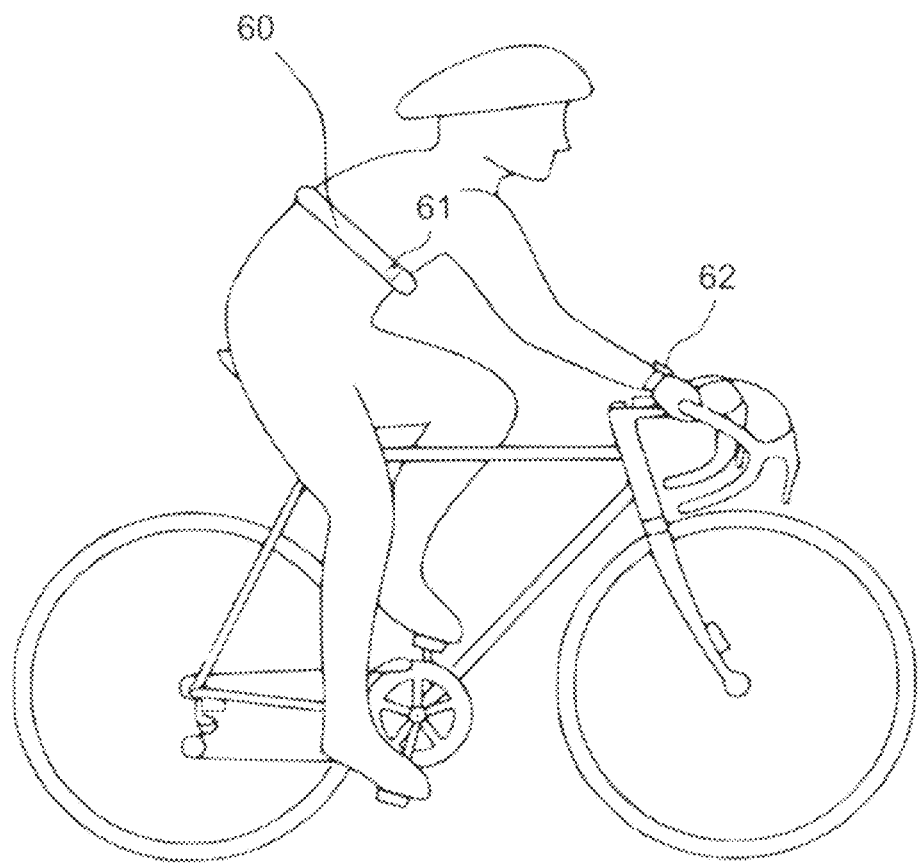
FIG. 6 illustrates an application system example according to at least some embodiments of the present invention.

FIG. 6 illustrates an example application system according to an embodiment. The system for heartrate monitoring of an object 60 comprises means for measuring the heartbeats of the object in a first unit 61. The first unit 61 may comprise at least some aspects of the apparatus illustrated above, such as the circuit illustrated in FIG. 4. The system further comprises means for determining a heartrate and transmitting the heartrate information wirelessly to a second unit 62 for further analyzing, or determining a time difference between consecutive heart beats and transmitting the time difference information wirelessly to the second unit 62 for further analyzing, or determining a time of each heart beat (time stamp) and transmitting the information of the time (time stamp) of each heart beat wirelessly to the second unit 62 for further analyzing. These means may also be arranged in the first unit, for example by the processor 51 and the communications unit 53.

The second unit 62 of the system may comprises a wristop computer, a mobile phone, a PDA, a sports equipment computer, a wearable or other type of computing device for further processing of the heartrate information. The second unit 62 may be configured to analyze if the time intervals between consecutive heart beats have varied below or above a certain minimum or maximum tolerance value. The second unit may inter alia e.g. calculate the difference in consecutive pulse intervals. The second unit may also be configured to control the first unit 61.

Heartrate information may be displayed on the display of the second unit 62. The pulse data of the person may be also stored on the second unit 62. The system may be used to measure not only pulse, but also, for example, blood pressure, speed, acceleration, distance travelled, and direction data.

The system for heartrate monitoring is powered by a power source, such as a battery. The power source may be a lithium ion rechargeable battery, for example. The power source may have an accessible port for recharging. An alternative example power source is e.g. an AA or AAA disposable or rechargeable battery. In some embodiments an energy harvesting collector is employed to power the system or a part thereof, such as the at least a part of the apparatus or circuit illustrated above in connection with FIG. 4. For example, application of new semiconductor materials, such as new class III-V semiconductors, may enable very low current consumption.

Figure 7:
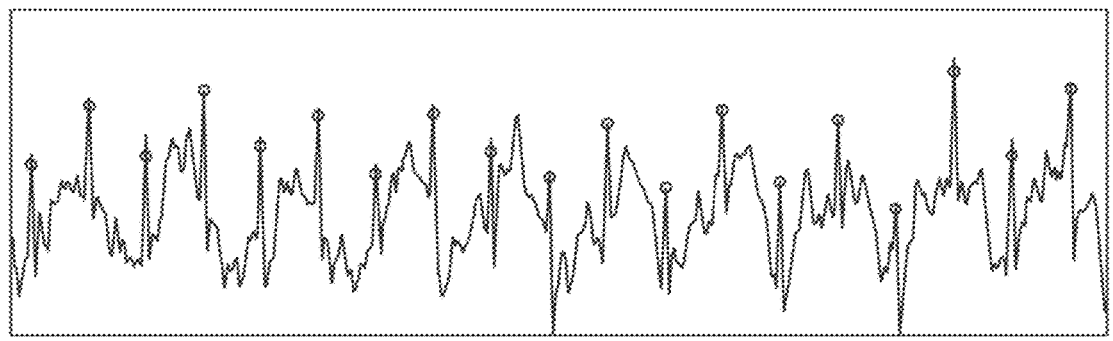
FIGS. 7 and 8 illustrate simulation results of the method and apparatus according to some embodiments.
Figure 8:
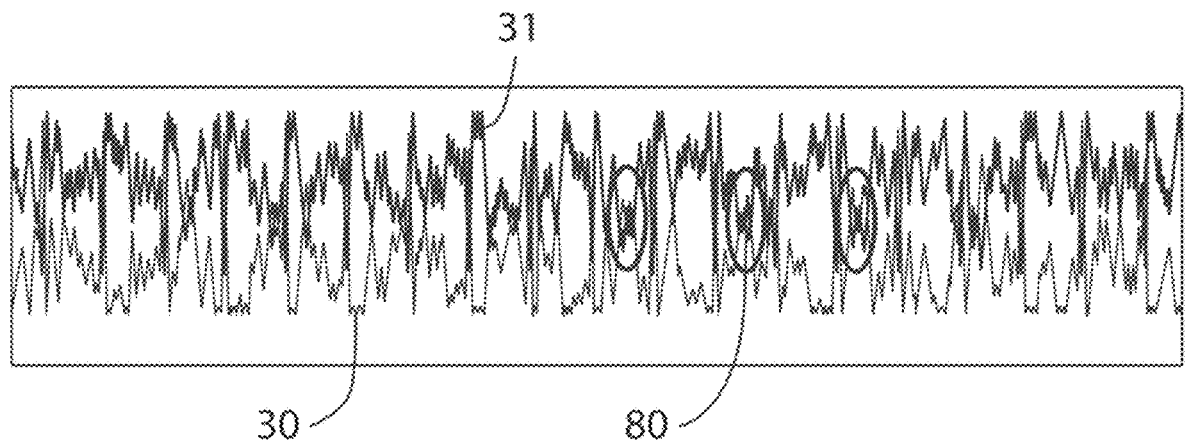

FIGS. 7 and 8 illustrate simulation results of the method and apparatus according to some embodiments. FIG. 7 illustrates a test signal measured while the tested person was running at speed 6-12.5 km/h. Small circles indicate detected spikes. In FIG. 8, generated on the basis of the test signal of FIG. 7, the first signal 30 is indicated by thinner line and the third signal 31 by bolded line. It can be seen that R wave spikes can be detected even if they would be under general level of the signal. FIG. 8 also shows by oval markings some situations 80 where the first signal and the third signal overlap. By above-illustrated S wave confirmation such false R wave indications may be avoided.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In this description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", that is, a singular form, throughout this document does not exclude a plurality.

INDUSTRIAL APPLICABILITY

At least some embodiments of the present invention find industrial application in devices for heartrate monitoring.

ACRONYMS LIST

ASIC Application-specific integrated circuit
DC Direct current
ECG Electrocardiogram
FPGA Field-programmable gate array
GSM Global system for mobile communication
LTE Long term evolution
NFC Near-field communication
N-RAT 3GPP new radio access technology
UI User interface
WCDMA Wideband code division multiple access,
WiMAX Worldwide interoperability for microwave access
WLAN Wireless local area network

The invention claimed is:

1. An apparatus for heartbeat detection, comprising:
   circuitry configured to form a first amplified signal and a second amplified signal on the basis of an input signal representative of heartbeat,
   circuitry configured to form a third signal by inverting the second signal and adding a base voltage, and
   circuitry configured to indicate an overlap of the first signal and the third signal for detecting R wave.

2. The apparatus of claim 1, wherein the circuitry configured to form the first amplified signal and the second amplified signal comprises:
   a first amplifier for amplifying an input heartbeat signal, and
   a second amplifier connected to an output of the first amplifier.

3. The apparatus of claim 2, wherein the circuitry configured to form the third signal comprises a third amplifier connected to an output of the first amplifier and to a base voltage source.

4. The apparatus of claim 3, wherein the circuitry configured to indicate the overlap comprises a first comparator connected to an output of the second amplifier and to an output of the third amplifier, wherein the first comparator is configured to indicate in the output of the first comparator R wave in response to the overlap.

5. The apparatus of claim 1, further comprising circuitry configured to detect an S wave on the basis of the third signal and indicating the S wave for confirming the R wave detection.

6. The apparatus of claim 4, further comprising circuitry configured to detect an S wave on the basis of the third signal and indicating the S wave for confirming the R wave detection, wherein the circuitry configured to detect the S wave comprise a second comparator connected to the output of the third amplifier and a reference voltage source providing a threshold voltage for detecting an S wave exceeding the threshold voltage.

7. The apparatus of claim 1, wherein the apparatus further comprises a processor connected to the circuitry configured to indicate the overlap, wherein the processor is configured to detect start time and end time of R wave on the basis of the indication of the overlap.

8. The apparatus of claim 6, further comprising a processor connected to the circuitry configured to indicate the overlap, wherein the processor is configured to detect start time and end time of R wave on the basis of the indication of the overlap and wherein the processor is connected to the output of the second comparator, the processor being further configured to:
   detect time of S wave on the basis of the indication from the second comparator,
   confirm the R wave in response to the S wave being detected within a predetermined time period after the R wave indication.

9. The apparatus of claim 8, wherein the processor is configured to define occurrence time of the R wave in the middle of the start time and the end time indication from the first comparator and store the occurrence value after the confirmation.

10. The apparatus of claim 1, further comprising:
    circuitry configured to determine heartrate on the basis of the indication of an overlap of the first signal and the third signal for detecting r wave, and
    an electrode element,
    wherein the input signal representative of heartbeat is sourced from the electrode element.

11. A method comprising:
    forming, via circuitry, a first amplified signal and a second amplified signal on the basis of an input signal representative of heartbeat,
    forming, via circuitry, a third signal by inverting the second signal and adding a base voltage, and
    indicating, via circuitry, an overlap of the first signal and the third signal for detecting R wave.

12. The method of claim 11, wherein the second amplified signal is formed by a first amplifier for amplifying an input heartbeat signal and the first amplified signal is formed by a second amplifier connected to an output of the first amplifier.

13. The method of claim 12, wherein the third signal is formed by a third amplifier connected to an output of the first amplifier and to a base voltage source.

14. The method of claim 13, wherein the overlap is indicated by a first comparator connected to an output of the second amplifier and to an output of the third amplifier, wherein the first comparator indicates R wave in response to the overlap.

15. The method of claim 11, wherein an S wave is detected on the basis of the third signal and indicated for confirming the R wave detection.

16. The method of claim 13, wherein the overlap is indicated by a first comparator connected to an output of the second amplifier and to an output of the third amplifier, wherein the first comparator indicates R wave in response to the overlap and wherein a second comparator connected to the output of the third amplifier and a reference voltage source providing a threshold voltage detects an S wave exceeding the threshold voltage.

17. The method of claim 11, wherein a processor detects start time and end time of R wave on the basis of the indication of the overlap.

18. The method of claim 16, wherein a processor detects start time and end time of R wave on the basis of the indication of the overlap and wherein the processor detects time of S wave on the basis of the indication from the second comparator and confirms the R wave in response to the S wave being detected within a predetermined time period after the R wave indication.

19. A heartrate monitoring system comprising an apparatus and a second unit wirelessly connectable to the apparatus for transmitting information indicative of heart beats from the apparatus to the second unit, the apparatus comprising:

circuitry configured to form a first amplified signal and a second amplified signal on the basis of an input signal representative of heartbeat, circuitry configured to form a third signal by inverting the second signal and adding a base voltage, and circuitry configured to indicate an overlap of the first signal and the third signal for detecting R wave.

20. A non-transitory computer readable medium having stored thereon a computer program comprising code, when executed in a data processing apparatus, to cause a method to be performed, said method comprising:

forming a first amplified signal and a second amplified signal on the basis of an input signal representative of heartbeat, forming a third signal by inverting the second signal and adding a base voltage, and indicating an overlap of the first signal and the third signal for detecting R wave.

* * * * *